(12) United States Patent
Mazellier

(10) Patent No.: US 8,999,127 B2
(45) Date of Patent: Apr. 7, 2015

(54) BIOLOGICAL SENSOR MEASURING ELECTROCHEMICAL AND/OR ELECTRICAL AND DIAMOND ELECTRODE AND ELECTRONIC INTEGRATED CIRCUIT

(75) Inventor: Jean-Paul Mazellier, Voiron (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 764 days.

(21) Appl. No.: 12/980,786

(22) Filed: Dec. 29, 2010

(65) Prior Publication Data

US 2011/0162962 A1 Jul. 7, 2011

(30) Foreign Application Priority Data

Dec. 30, 2009 (FR) ...................................... 09 59675

(51) Int. Cl.
| | | |
|---|---|---|
| *G01N 27/403* | (2006.01) | |
| *G01N 27/414* | (2006.01) | |
| *H01L 29/16* | (2006.01) | |
| *H01L 21/04* | (2006.01) | |
| *H01L 29/78* | (2006.01) | |

(52) U.S. Cl.
CPC ........ *H01L 29/1602* (2013.01); *H01L 21/0425* (2013.01); *H01L 29/78* (2013.01); *G01N 27/4145* (2013.01); *G01N 27/4148* (2013.01)

(58) Field of Classification Search
CPC ........... C12Q 2565/607; G01N 27/414; G01N 27/4145; G01N 27/4148; H01L 2924/1433; H01L 29/66; H01L 24/82; H01L 2924/13091; H01L 21/0425; H01L 23/53295; H01L 25/0657; H01L 51/0508; H01L 51/0512

USPC .......... 204/403.15; 438/1; 257/253, E29.255, 257/E21.409

See application file for complete search history.

(56) References Cited

U.S. PATENT DOCUMENTS

| | | | |
|---|---|---|---|
| 5,777,372 A | 7/1998 | Kobashi | |
| 6,484,559 B2 * | 11/2002 | Dodabalapur et al. | ....... 73/23.34 |
| 6,913,999 B2 * | 7/2005 | Searls et al. | ................... 438/667 |
| 7,244,963 B2 | 7/2007 | Ravi | |

(Continued)

FOREIGN PATENT DOCUMENTS

| | | |
|---|---|---|
| JP | 5-18935 | 1/1993 |
| JP | 8-240555 | 9/1996 |
| KR | 10-2009-0094631 | 9/2009 |

OTHER PUBLICATIONS

U.S. Appl. No. 12/980,760, filed Dec. 29, 2010, Mazellier.

(Continued)

*Primary Examiner* — Alex Noguerola
(74) *Attorney, Agent, or Firm* — Oblon, McClelland, Maier & Neustadt, L.L.P.

(57) ABSTRACT

A biological sensor for electrochemical and/or electrical measurement, including at least:
a measurement electrode, able to make electrochemical and/or electrical measurements, and including a part of a doped diamond layer of a substrate comprising a stack including a dielectric layer placed between the doped diamond layer and a semiconductor material layer;
an electronic circuit for amplifying and/or processing at least one electrical signal intended to be issued by the measurement electrode, electrically connected to the measurement electrode and made in a portion of the semiconductor material layer.

11 Claims, 7 Drawing Sheets

(56) References Cited

U.S. PATENT DOCUMENTS

Figure 1A:
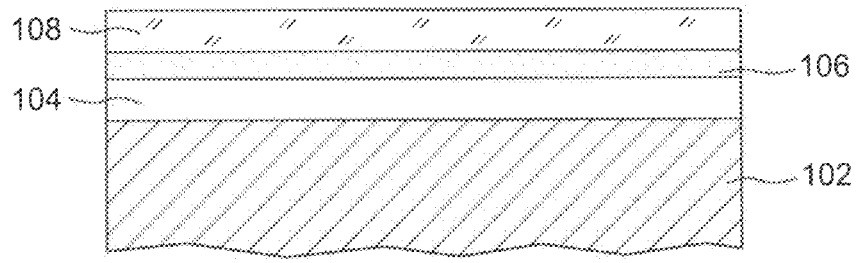

| | | | |
|---|---|---|---|
| 2008/0237718 | A1 | 10/2008 | Noveski et al. |
| 2008/0308846 | A1* | 12/2008 | Shim et al. .................... 257/253 |
| 2009/0301900 | A1* | 12/2009 | Einaga et al. ............. 205/780.5 |
| 2010/0065892 | A1 | 3/2010 | Hwang et al. |
| 2010/0116655 | A1* | 5/2010 | Harley et al. ............ 204/403.01 |
| 2010/0252884 | A1* | 10/2010 | Kitano .......................... 257/348 |
| 2010/0294672 | A1* | 11/2010 | Gahr et al. .................... 205/786 |
| 2011/0104862 | A1* | 5/2011 | Kadoya ......................... 438/270 |

OTHER PUBLICATIONS

U.S. Appl. No. 13/055,793, filed Jan. 25, 2011, Mazellier et al.

Preliminary Search Report issued Jul. 28, 2010 in France Application No. FA 730493 (With Translation of Category of Cited Documents).

Byungchul Jang, et al., "Biosensor Systems in Standard CMOS Processes: Fact or Fiction?" IEEE Transactions on Industrial Electronics, vol. 56, No. 4, Apr. 2009, pp. 979-985.

Jiang Wang, et al., "Covalent immobilization of glucose oxidase on conducting ultrananocrystalline diamond thin films", Diamond and Related Materials, vol. 15, No. 2-3, Feb. 1, 2006, pp. 279-284.

J. K. Luo, et al., "Diamond and diamond-like carbon MEMS", Journal of Micromechanics and Microengineering, Institute of Physics Publishing, vol. 17, No. 7, Jul. 1, 2007, pp. S147-S163.

A. V. Sumant, et al., "Large Area Low Temperature Ultrananocrystalline Diamond (UNCD) Films and Integration with CMOS Devices for Monolithically Integrated Diamond MEMS/NEMS-CMOS Systems", Proc. SPIE: Micro-and Nanotechnology Sensors, Systems and Applications, vol. 7318, Apr. 19, 2009, pp. 1-7.

Orlando Auciello, et al., "Are Diamonds a MEMS' Best Friend?", IEEE Microwave Magazine, IEEE Service Center, vol. 8, No. 6, Dec. 1, 2007, pp. 61-75.

Arun Manickam, et al., "A CMOS Electrochemical Impedance Spectroscopy Biosensor Array for Label-Free Biomolecular Detection", Solid-State Circuits Conference Digest of Technical Papers (ISSCC), 2010 IEEE International, Feb. 7, 2010, pp. 130-131.

Wensha Yang, et al., "Fabrication and characterization of a biologically sensitive field-effect transistor using a nanocrystalline diamond thin film", Applied Physics Letters, AIP, American Institute of Physics, vol. 85, No. 16, Oct. 18, 2004, pp. 3626-3628.

Nikos Chaniotakis, et al., "Novel semiconductor materials for the development of chemical sensors and biosensors: A review", Analytica Chimica Acta, Elsevier, vol. 615, No. 1, May 12, 2008, pp. 1-9.

Christoph E. Nebel, et al., "Diamond and biology", Journal of the Royal Society Interface, 4, 2007, pp. 439-461.

Arjang Hassibi, et al., "A Programmable 0.18-μm CMOS Electrochemical Sensor Microarray for Biomolecular Detection", IEEE Sensors Journal, vol. 6, No. 6, Dec. 2006, pp. 1380-1388.

Wensha Yang, et al., "DNA-modified nanocrystalline diamond thin-films as stable, biologically active substrates", Nature Materials, vol. 1, Dec. 2002, pp. 253-257.

Yue Huang, et al., "Post-CMOS Compatible Microfabrication of a Multi-Analyte Bioelectrochemical Sensor Array Microsystem", IEEE International Conference on Sensors, Oct. 22-25, 2006, pp. 612-615.

Peter M. Levine, et al., "Active CMOS Sensor Array for Electrochemical Biomolecular Detection", IEEE Journal of Solid-State State Circuits, vol. 43, No. 8, Aug. 2008, pp. 1859-1871.

Anita Karegar, "Electrochemical, Multi-analyte Biosensor Array for Neurotransmitter Detection", Colorado State University, 2007, pp. 1-49.

Paul W. May, "Diamond thin films: a 21st-century material", Phil. Trans. R. Soc. London, A, 358, 2000, pp. 473-495.

D. Das, et al., "A review of nucleation, growth and low temperature synthesis of diamond thin films", International Materials Reviews, 2007, vol. 52, No. 1, pp. 29-64.

Office Action issued Dec. 17, 2013 to Japanese Patent Application No. 2010-290522, with English translation.

\* cited by examiner

US 8,999,127 B2

BIOLOGICAL SENSOR MEASURING ELECTROCHEMICAL AND/OR ELECTRICAL AND DIAMOND ELECTRODE AND ELECTRONIC INTEGRATED CIRCUIT

TECHNICAL FIELD

The invention concerns a biological sensor, also called a biosensor, for electrical detection, able especially to be used for portable PoC (Point of Care) type biological detection applications, and capable of making measurements and/or detection of molecules in vivo and/or in vitro for electrochemical and/or electrical detection of these molecules.

The invention applies, for example, to the fields of medical care, nutrition, industrial treatments, and environmental monitoring, to detect pollutants, microorganisms, proteins, electrical signals, etc.

STATE OF THE PRIOR ART

A biosensor is a measuring device converting a biochemical phenomenon into a measurable signal, such as an optical or electrical signal. Some of these biosensors use a principle called "key-lock": in this type of biosensor, a functional surface of the biosensor, meaning a surface on which the biological receptors adapted to the molecules that one intends to detect, have been grafted, is immersed in a solution to be analyzed. If these biological molecules that one intends to detect, meaning molecules that are complementary to the grafted receptors, are in the solution, an interaction and binding of the molecules to the receptors occurs. The biosensor, then, detects the presence of these molecules which are complementary to the previously grafted receptors.

These molecules may be detected optically, by fluorescence, for example. In this case, either the molecule to be detected is naturally fluorescent, or it is appropriate to make them fluorescent by grafting markers on them. The presence of molecules attached to the receptors is then detected by lighting the functional surface of the biosensor by laser, each marker having a specific response. Then, the response in fluorescence is detected spatially, by which one may deduce the presence or absence of the molecules to be detected. Various optical properties (absorption spectrum, bioluminescence, etc.), which are not the fluorescence, may also be used to detect the molecules.

Optical detection of the molecules particularly has the advantages of offering good selectivity due to the double detections performed (target receptor and target marker) and allowing the simultaneous detection of different types of molecules (detection of several target/molecules present in the same solution, by different functions in the surface of the biosensor), for instance when the biosensor is a DNA chip.

However, such optical detection of molecules also has several drawbacks:
- functioning of the surface requires constrained preparation;
- marking of the molecules to be detected adds constrained operations and poses problems of reactivity due to the time necessary to effect the marking;
- necessary detection instrumentation is constraining and incompatible with the production of a portable biosensor.

Alternatively, detection of the molecules may be done electrically, in a faradaic manner (charge transfer across an interface, such as by measuring impedance, etc.) or non-faradaic (use of displacement currents or electrostatic effects).

Other biosensors, called "electrochemical biosensors", are based on redox (oxidation-reduction) reactions of the molecules to be detected. This electrochemical method is a purely electrical method, in which the molecules intended to react electrochemically with the molecules to be detected are grafted onto an analysis electrode of the biosensor, the electrical response of the molecules being, thus, detected. These electrochemical biosensors are based on an amperometric or potentiometric detection of the molecules.

Amperometric detection is a technique based on the determination of the intensity of a current which crosses an electrochemical cell at a potential imposed between two of the biosensor's electrodes. This current intensity is a function of the concentration of the electroactive bodies, which will be oxidized or reduced on one of the two electrodes, called measurement electrode or measuring electrode, the second electrode serving as a reference electrode.

Potentiometric detection is an electrochemical method based on measuring a potential difference between a measurement electrode and reference electrode. Two types of potentiometric detection can be used. The first uses a measurement electrode (ISE, or "Ion Selective Electrode") to which are attached bioreceptors and a second reference electrode, the potential of the measurement electrode varies when the analyte (molecules that to be detected) reacts with the bioreceptors attached to the measurement electrode. The second uses field effect transistors (FET), which are sensitive to the charges on the surface of the transistor grids. By modifying the grids on an ISE, we get an ISFET, or ion sensitive field effect transistor.

There are also electrochemical sensors that make measurements by electrochemical impedance spectroscopy (EIS). For this, a weak sinusoidal excitation is superimposed on a constant excitation involving a variation of the current at the same frequency. The voltage/current ratio (complex) then gives the impedance (complex) of the system.

Thus, compared to biosensors performing optical detection of the molecules, electrochemical biosensors do not require molecule marking. Furthermore, these biosensors can make measurements in real time, be manufactured at a low costs by standard microelectronic processes, are compact, flexible in use, and allow mutliplexing of the detections conducted.

However, electrochemical biosensors from prior art also have various drawbacks:
- they have a weak gain in transduction, which reduces detection limits;
- they require preparation of the electrode surfaces, and use electrochemical interfering elements (active ionic species);
- they introduce heat sources, of electronic origin, close to the media to be analyzed, which may be critical for biological media that are very sensitive to temperatures.

U.S. Pat. No. 5,777,372 describes the use of diamond based structure replacing the metal electrodes in the sensors. Diamond especially has the advantage of being very resistant to most chemical agents, is non-corrosive, and offers windows of activity superior to those of platinum, as an example. The window of activity of a material is the extent of the range of voltages usable in aqueous media. For potentials beyond this window, a redox reaction occurs from the water (media) on the electrodes, preventing it from detection any other reaction. A comparison of the windows of activity of various materials, including diamonds, is described in the document from C. E. Nebel et al., "Diamond and biology". Journal of the Royal Society Interface, 4, pages 439-461, 2007.

Such a biosensor has the additional drawback that the electronic measurement from the biosensor is formed by an external analyzer which is connected to the biosensor. The shielding necessary for the measurement poses a problem, because, given the very weak current levels (in the picoamp range), it becomes necessary to insert the biosensor into a performing Faraday cage. Furthermore, significant constraints are imposed on the quality of the cables and connections, since the signal is only amplified after arriving at the analyzer.

DESCRIPTION OF THE INVENTION

Thus there is a need to propose a new type of biological sensor with the advantages of biosensors using diamond-based electrodes, but which does not have the drawbacks of biosensors in which the measurement electronics are offset by the rest of the biosensor.

For this, one embodiment proposes a biological sensor, or biosensor, for electrochemical and/or electrical measurement, including at least:
- an electrode, such as a measurement electrode or measuring electrode, able to make electrochemical and/or electrical measurements, and including at least a part of a doped diamond layer of a substrate comprising a stack including at least one dielectric layer placed between the doped diamond layer and a semiconductor material layer.
- an electronic circuit for amplifying and/or processing at least one electrical signal intended to be issued by the measurement electrode, electrically connected to the measurement electrode and made in a portion of the semiconductor material layer.

This sensor applies a detection principle based on electrochemical and/or electric measurements (potentiomtery, cyclic voltametry, amperometry, etc.) which can be applied to biology, either by direct interaction (measurement of redox couples, potentials) or by a key-lock type interaction when the measurement electrode includes biological receptors grafted to it.

This sensor uses at least a portion of a doped diamond layer as a measurement electrode serving as an electrical and chemical interface between a medium to be analyzed (biologically and/or chemically) and an amplification and/or processing electronic circuit. The electronic circuit is, thus, integrated with the remainder of the sensor, especially with the sensor electrode(s). The term "processing" indicates any type of operation conducted on the electrical signal issued by the electrode: reading, scanning, etc.

The use of doped diamond as a biological interface entails the benefit of various advantages in this material: biocompatibility, non-toxicity, large electrochemical window, low noise, etc. Coupling and integrating the diamond with the electronic circuit allows reducing the size of the sensor and increasing its sensitivity, since the sensor can be easily isolated from external noise sources. Furthermore, in this sensor, the electronic circuit allows for integrated amplification, closer to the measurement made by the measurement electrode. Moreover, such a sensor allows the making of a computer interface (by the electronic circuit) for portable applications.

Also, in this biosensor, the signal is amplified and/or processed "at the source", which limits the effects of noise from the wiring and the environment.

The substrate may be of the SOD (semiconductor on diamond) type. In this case, due to the semiconductor material layer and the diamond layer being part of the same SOD substrate, the sensor has at least one electrode made in a doped diamond layer physically connected to a semiconductor layer in which the electronic circuit is built, these two layers forming, thus, a single block.

The dielectric layer placed between the diamond layer and the semiconductor layer especially enable protection of the diamond from oxygen flows at high temperatures, used in the making of the electronic circuit, since the diamond is very sensitive to the presence of oxygen at high temperatures (it oxidizes at 600° C. in the presence of $O_2$). Additionally, this dielectric layer also allows electrical insulation of the electrodes from the biosensor vis-a-vis the semiconductor layer, and, prevents, thus, electrical interactions between the electrodes and the electronic circuit.

The semiconductor material layer may have a thickness less than or equal to around 1 µm; The electronic circuit may have one or more PD-SOI (partially depleted semiconductor on insulation) or FD-SOI (fully depleted semiconductor on insulation) transistors. Such transistors especially have the advantages of low consumption, low noise capacity, and low intrinsic noise.

The measurement electrode may be delimited from the remainder of the diamond layer by trenches filled with at least one dielectric material and passing through, or crossing, at least the diamond layer. These trenches may isolate the measurement electrode from the rest of the diamond layer, but also protect the diamond forming the electrode from oxygen flows during the making of the electronic circuit.

The electronic circuit may be electrically connected to the measurement electrode by through vias and at least one electrical interconnection layer composed of at least one electrically conductive material made into at least one passivation layer composed of at least one dielectric materials, the semiconductor material layer being placed between the diamond layer and the passivation layer.

The passivation layer, which may also be a multi-layer formed by several superimposed passivation layers, may be placed between a massive layer able to form a mechanical support for the sensor and the semiconductor layer. Thus, the diamond layer may form nearly the entirety of the surface of the sensor exposed to the medium to be analyzed.

In one variant, at least one hole made through at least the passivation layer, the semiconductor layer, and the dielectric layer may provide access to the measurement electrode.

The electronic circuit may be electrically connected to the measurement electrode by through vias and at least one electrical interconnection layer composed of at least one electrically conductive material formed in at least one passivation layer composed of at least one dielectric material placed against the semiconductor materials, and in which at least one hole made through at least the passivation layer provides an access to the measurement electrode. Here, again, the passivation layer may also be a multi-layer formed by several passivation layers superimposed one over the other.

The measurement electrode may be placed in a recess formed at least in the semiconductor layer.

Biological receptors which are complementary to the molecules intended to be detected by the sensor, may be grafted onto the measurement electrode. Thus, the sensor may use the "key-lock" principle of detection. Furthermore, it is also possible for markers of the target molecules to be used, in order to increase the selectivity of the key-lock process, limiting the parasitic effects related to the detection of wrong targets.

The sensor may include, also, a second electrode forming a reference electrode, or a second and third electrode, forming respectively a reference electrode and a counter-electrode, each electrode of the sensor able to include at least a portion of the diamond layer. Thus, the sensor may include all of these doped diamond based electrodes integrated with the rest of the sensor, and, especially, with the electronic circuit. When the sensor has two electrodes, measurement of the difference in potential between the measurement electrode and the reference electrode allows direct measurement of the concentration of the analyte sought. When the sensor has three electrodes, voltage between the working electrode, on which the reaction of interest takes place, and the counter-electrode, may be adjusted by establishing an input voltage from the desired cell between the working electrode and the reference electrode. It is also possible to have other methods of use for such a sensor with two or three electrodes. Furthermore, it is possible for the sensor to have more than three electrodes.

It is also proposed a production method of a biological sensor for electrochemical and/or electrical measurements with at least the following steps:
- making of an electrode, such as a measurement electrode, able to make electrochemical and/or electrical measurements, and including at least a part of a doped diamond layer of a substrate comprising a stack including at least one dielectric layer placed between the doped diamond layer and a semiconductor material layer;
- making, in a portion of the semiconductor material layer, of an electronic circuit for amplifying and/or processing an electrical signal intended to be issued by the measurement electrode;
- making of an electrical connection at least between the measurement electrode and the electronic circuit.

The making of the measurement electrode may be achieved by implementation of at least the following steps:
- etching of trenches at least through the diamond layer, the semiconductor layer, and the dielectric layer, able to delimit a portion of the diamond layer intended to form the measurement electrode.
- filling of the trenches with at least a dielectric material.

The dielectric layer placed between the semiconductor layer and the diamond layer, as well as the dielectric material placed in the trenches, may protect the portion of the doped diamond layer forming the measurement electrode from high temperature oxygen flows able to be used in the making of the electronic circuit.

The making of the electrical connection between the measurement electrode and the electronic circuit may be achieved by the implementation of at least the following steps:
- depositing at least one passivation layer composed of at least one dielectric material on the semiconductor material layer, able to cover the electronic circuit;
- making of through vias composed of at least one electrically conductive material electrically connected to the measurement electrode and to the electronic circuit through at least the passivation layer,
- making of an electric interconnection layer composed of at least one electrically conductive material on the passivation layer, such that at least a portion of the electrical interconnections layer and the through vias may electrically connect the measurement electrode to the electronic circuit.

The method may include, additionally, after the making of the electrical connection between the measurement electrode and the electronic circuit, a step of depositing at least a second passivation layer covering at least the electrical interconnection layer, then a step for securing the second passivation layer with a massive layer forming a mechanical support for the sensor.

In one variant, the method may also include, after the making of the electrical connection between the measurement electrode and the electronic circuit, a step for etching at least one hole through at least the passivation layer, the semiconductor material layer, and the dielectric layer, providing access to the measurement electrode.

Making of the measurement electrode may be achieved by implementing at least one step of etching the diamond layer.

The making of the measurement electrode may be achieved by the implementation of at least a step of depositing the diamond layer on the dielectric layer, the diamond layer and at least a portion of the dielectric layer able to be placed in a recess formed at least in the semiconductor material layer.

The method may include, additionally, between the step of making the measurement electrode and the step of making the electronic circuit, a step of etching the dielectric layer, such that at least a remaining portion of the dielectric layer may be placed between the measurement electrode and the semiconductor layer, then, a step of depositing a dielectric material able to cover at least the measurement electrode.

The making of the electrical connection between the measurement electrode and the electronic circuit may be achieved by the implementation of at least the following steps:
- depositing at least one passivation layer composed of at least one dielectric material on the semiconductor material layer, able to cover the electronic circuit and the measurement electrode.
- making of through vias composed of at least one electrically conductive material electrically connected to the measurement electrode and the electronic circuit through at least the passivation layer,
- making of an electrical interconnection layer composed of at least one electrically conductive material on the passivation layer, such that at least a portion of the electrical interconnection layer and the through vias may electrically connect the measurement electrode to the electronic circuit.

The method may further comprise, after the making of the electrical connection between the measurement electrode and the electronic circuit, a step of etching at least one hole through at least the passivation layer, providing an access to the measurement electrode.

The step(s) implemented for the making of the measurement electrode may also produce a second electrode serving as, or forming, a reference electrode, or a second and third electrode serving, respectively, as, or forming, a reference electrode and a counter-electrode, each electrode of the sensor able to include at least a portion of the diamond layer.

The method may include, additionally, a step for grafting biological receptors complementary to the molecules intended to be detected by the sensor on the measurement electrode.

BRIEF DESCRIPTION OF THE DESIGNS

Figure 1B:
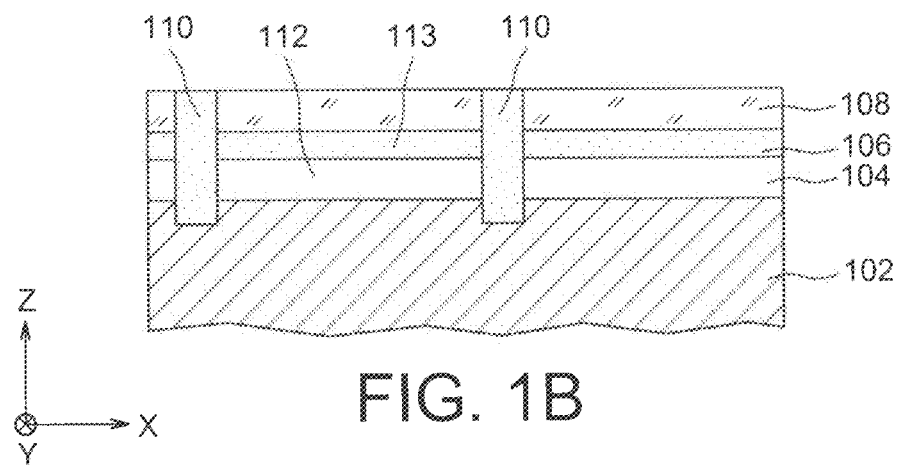
Figure 1C:
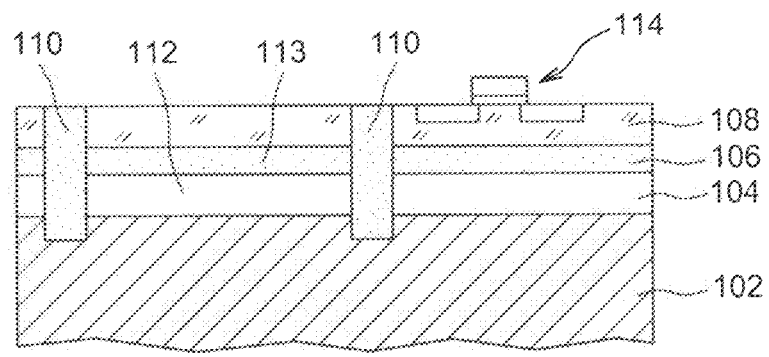
Figure 1D:
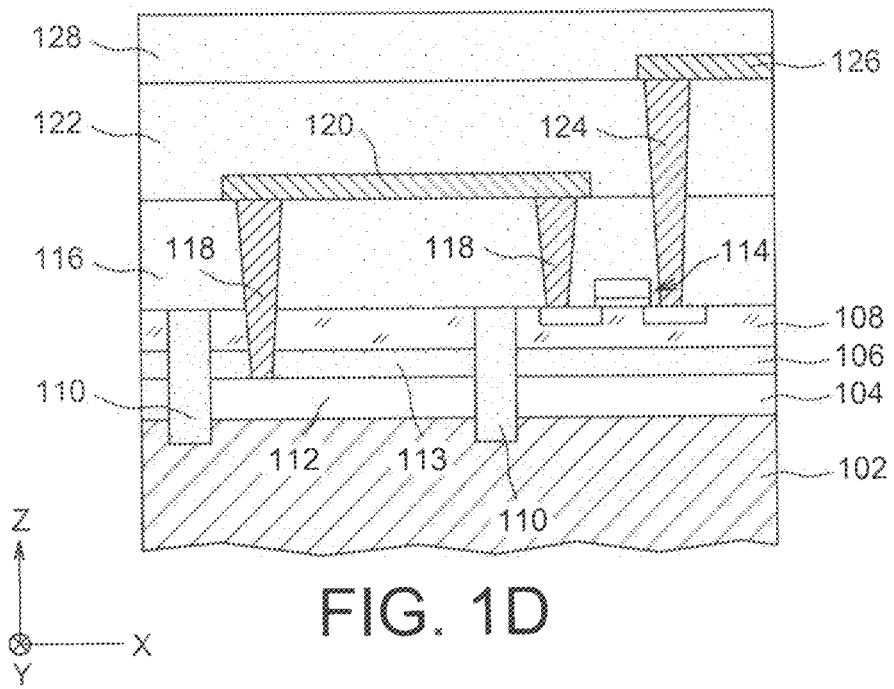
Figure 1E:
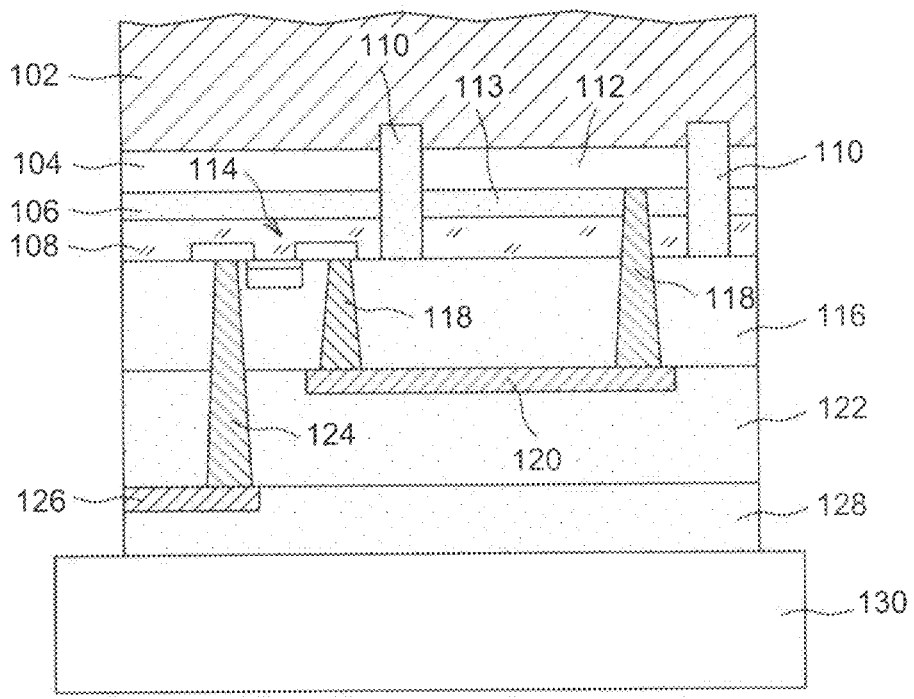
Figure 1F:
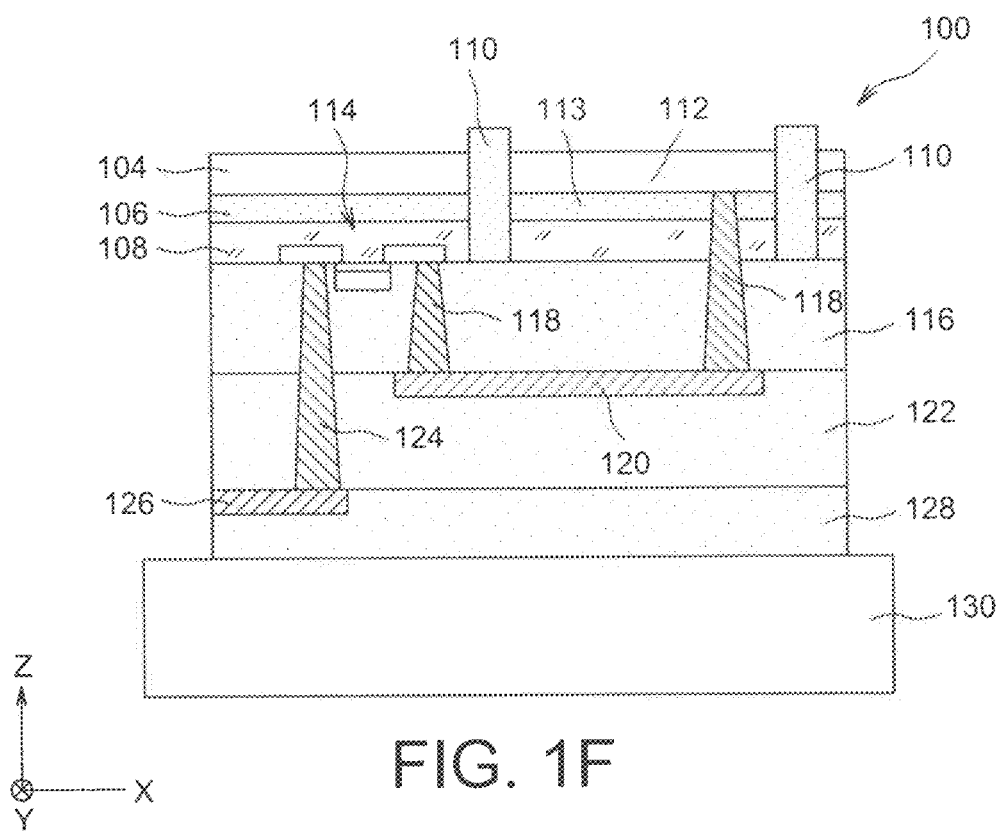
Figure 1G:
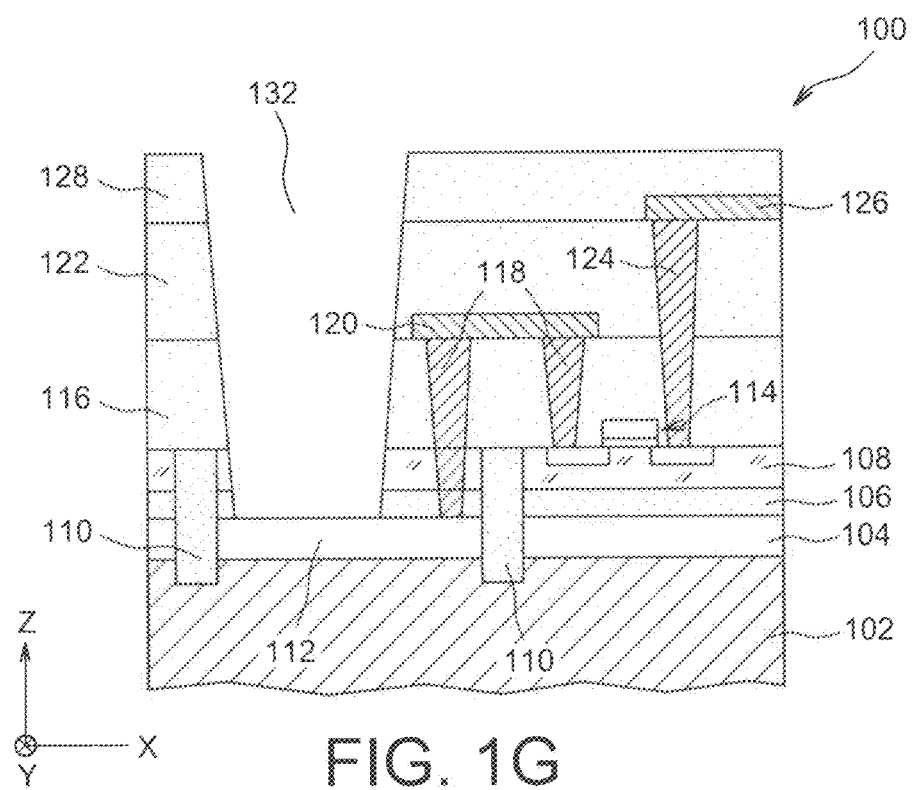

This invention will be best understood by reading the description of example constructions given for purely indicative purposes, and not limiting, making reference to the attached designs on which:

FIGS. 1A to 1F show the steps of a method for production of a biological sensor according a first embodiment, FIG. 1G shows a biological sensor according to a variant of the first embodiment, FIGS. 2A to 2D show the steps of a method for production of a biological sensor according to a second embodiment, FIGS. 3A to 3D show the steps of a method for production of a biological sensor according to a third embodiment.

Identical, similar, or equivalent parts from the different figures described below carry the same numerical references in order to facilitate transition from one figure to another.

The different parts shown in the figures are not necessarily shown to scale, uniformly, in order to make the figures more easily readable.

The various possibilities (variants and embodiments) must be understood as not being exclusive of each other, and able to be combined together.

DETAILED DESCRIPTION OF THE SPECIFIC EMBODIMENTS

First we refer to FIGS. 1A to 1F, which show the steps of a method of making a biological sensor 100, or biosensor, for electrochemical and/or electrical measurement, according to a first embodiment. In these FIGS. 1A to 1F, only the production of part of the biosensor 100 is shown.

As shown in FIG. 1A, the biosensor 100 is made of a SOD substrate, meaning a semiconductor on diamond type substrate, including a back layer 102 serving as a mechanical support, a doped diamond layer 104, a barrier layer 6, and a surface layer 108 composed of a semiconductor, in this case, silicon.

The diamond layer 104 is placed between the backing layer 102 and the barrier layer 106, and the barrier layer 106 is placed between the diamond layer 104 and the surface layer 108.

The surface layer 108 is preferably a thin layer, with a thickness less than or equal to around 1 µm. The barrier layer 106 is composed of a dielectric material, such as an oxide of semiconductor or nitride of semiconductor (for example, $SiO_2$ or SiN), and has, for example, a thickness between around 50 nm and 1 µm. Both the material and the thickness of the barrier level 106 are selected in order to electrically insulate the diamond layer 104 from the semiconductor layer 108, but also to protect the doped diamond layer 104 from high temperature oxygen flows used during the later making of the electronic circuits in the surface layer 108. In fact, the diamond is oxidized at 600° C. However, the thermal processes implemented during the making of electronic circuits use oxygen at temperatures greater than or equal to about 600° C., for example during the formation of the transistor grid by thermal oxidation.

The doped diamond of the layer 104 may be of the CVD (chemical vapor deposited) polycrystalline type, HOD (highly oriented diamond), or even of the intrinsic monocrystalline type, and, for example, doped preferably with boron (type p) or phosphorous (type n). The thickness of the diamond layer 104 may be between around 100 nm and 1 µm.

Although it is not visible on FIG. 1A, the diamond layer 104 has a granular structure. In effect, synthetic diamond is generally formed on a heterosubstrate, meaning a substrate composed of a material other than diamond (silicon, here), which implies, giving the growth process used to form the diamond, that the diamond has a granular structure with development of grains in the direction of the thickness of the material (forming a column type diamond layer). However, the base of the grains, which is part of the diamond layer formed at the beginning of the diamond's growth, called the "nucleation part", meaning that which is against the substrate, is generally electrically defective due to the presence of a significant number of joints of grains, graphite, etc. This nucleation part may be located, preferably, on the side of the backing layer 102, or of the barrier layer 106.

Finally, the backing layer 102 is here a massive semiconductor layer, such as silicon based, of a thickness equal or greater than 10 µm.

The steps of making of such a SOD substrate are known in the state of the art (transfer of layers, molecular bonding, . . . ) and are therefore not detailed here.

Then, we make trenches 110, through the surface layer 108, the barrier layer 106, and the doped diamond layer 104, delimiting the active electrodes of the biosensor 100 in the doped diamond layer 104. These trenches 110 are also made in part of the backing layer 102. The biosensor 100 may include, for example, two or three electrodes (measurement electrode, reference electrode, counter-electrode). In the example showed in FIGS. 1A to 1F, only the measurement electrode, referenced 112, of the biosensor 100, is shown. These trenches 110 are, for example, made by etching through the entire thickness of layers 108, 106, 104, and part of the thickness of the backing layer 102, then, by filling these etched trenches 110 with a biocompatible dielectric materials, for example composed of a semiconductor oxide or semiconductor nitride (such as $SiO_2$ or SiN) or intrinsic diamond. One can see in FIG. 1B, that a portion 113 of the barrier layer 106, of dimensions substantially similar to those of the measurement electrode 112, is capable of protecting the measurement electrode 112 from high temperature oxygen flows used in the making of the electronic circuits in the surface layer 108. The material used the fill the trenches 110 is also chosen in order for it to serve as a barrier to the diffusion of high temperature oxygen for the measurement electrode 112 during the making of the electronic circuits in the surface layer 108.

Choice of the dimensions of the electrodes made in the doped diamond layer 104 is a function of the thickness of the diamond layer 104. The minimum dimension of an electrode, in the (X, Y) plane drawn in FIG. 1B, corresponding, for example, to the length of one side of the electrode when it is of a substantially rectangular shape, may be chosen significantly equal to the thickness of the diamond layer. Choosing the dimensions of the electrodes of the biosensor 100 will, however, take into account other considerations, such as the minimum signal amount to obtain for an electrode, the technological feasibility of producing tiny electrodes, etc. Thus, in general, the dimensions of the electrode may be chosen such that about one hundred grains of the doped diamond layer 104 are under one of the electrodes of the biosensor 100. The dimensions of the electrodes, in the (X, Y) plane, shown in FIG. 1B, are, for example, between around 10 µm and 100 µm.

We then make the electronic circuits of the biosensor 100, according to standard microelectronic process, in the surface layer 108. In FIG. 1C, a single MOS transistor in an electronic circuit 114 is shown. The electronic circuit 114 here serves as an amplifier of the electrical signal generated at the terminals of the electrodes of the biosensor 100. In this present example, the output of the electronic circuit 114 is connected to the input of a reading and digitization circuit that is common with that of other biosensors. In one variant, the electronic circuit 114 may, in addition to serving as an amplifier, serve for reading and/or digital/analog conversion of the signal. If the surface layer 108 is a thin layer, with a thickness of equal to or less than around 1 µm, the electronic circuit 114 may include elements, such as transistors, of PD-SOI type, that is with a partial depletion, or FD-SOI type, that is with a full depletion.

During the making of the electronic circuit 114, high temperature oxygen flows cross the surface layer 108, such during a step for oxidation of the semiconductor of the surface layer 108. The dielectric materials in the barrier layer 106 and the trenches 110 then protect the diamond layer 104 and the backing layer 102 from these oxygen flows which, in the absence of the barrier layer 106 and/or trenches 110 would cause combustion of the diamond and irreversible deterioration of the diamond layer 104.

Them we make the electrical interconnections at several layers, in order to electrically connect the doped diamond electrodes of the biosensor 100 to the electronic circuit 114. In the example in FIG. 1D, we first begin by depositing a first passivation layer 116, made of a dielectric material, covering the surface layer 108, and the electronic circuit 114. The through vias 118, made of an electrically conductive material, are then made through the passivation layer 116, the surface layer 108, and the barrier layer 106, and, in part in the measurement electrode 112, in order to electrically connect the electronic circuit 114 and the measurement electrode 112. Then, a first electrical connection layer 120, for example made of aluminum, and/or another suitable electrically conductive material, is made on the passivation layer 116, allowing electrical connection, through the vias 118, of the measurement electrode 112 to the electronic circuit 114. The electrical interconnections layer 120 is then covered by a second passivation layer 122. In the example in FIG. 1D, another through via 124 is made through the two passivation layers 116, 122 in order to electrically connect the electronic circuit 114. Although not shown, at least one other via is made through the passivation layers 116, 122, in order to electrically connect another element, such as another electrode of the biosensor 100. A second electrical interconnections layer 126 is then made on the second passivation layer 122, in order to electrically connect the electronic circuit 114 to said other element of the biosensor 100. The second electrical interconnections layer 126 is finally covered by a third passivation layer 128. The passivation layers 116, 122, and 128, are, for example, each of a thickness equal to around 400 nm.

In the example described above, the biosensor 100 includes two levels of electrical interconnections. However, the biosensor 100 may include a greater number of levels of interconnections, such as when the biosensor 100 has three electrodes. Furthermore, the passivation layers made may be viewed as a multilayer in which the various levels of electrical interconnections are made.

In order to make the electrochemical measurements with the active electrodes of doped diamond, we can remove portions of the backing layer 102 covering these electrodes in order to free them. This may be done by local etching of the backing layer 102 with deep trenches. In the example on FIG. 1D, this etching may be done at the level of the measurement electrode 112.

In one variant, and as is shown in FIGS. 1E and F, it is possible to remove the entire backing layer 102, allowing the device 100 to show flat surface in the majority of the diamond based part, increasing the biocompatibility of the biosensor 100 with the medium to be analyzed. For this, we transfer the elements previously made on a mechanical handle 130, for example made of glass or a semiconductor, by securing the passivation layer 128 to the mechanical handle 130 (FIG. 1E). This handle 130 may be provided to make electrical contact with the output of the electronic circuit 114 for extracting the measurements. In this case, the electrical contacts connected to the electrical interconnections layers previous made cross the handle 130 in order to be able to access these contacts from the side of the handle opposite that attached to the passivation layer 128.

Finally, as shown in FIG. 1F, once the passivation layer 128 is attached to the handle 130, we remove the backing layer 102, possibly by grinding or chemical corrosion, revealing the diamond layer 104.

In one variant, it is possible to structure the active, doped diamond based electrodes in points, such as by processing with oxygen plasma implemented with masking fitted over the electrodes (the mask being made, for example, of aluminum). Such electrodes are, for example, used to form matrices of points for probing neural networks (the form factor is important in this case). Such electrodes may be made from a diamond layer of a thickness equal to a few dozen microns, for example (for example, greater than around 20 µm).

As an alternative to the embodiment previously described in FIGS. 1A to 1F, it is possible to make the biological sensor 100 as shown in FIG. 1G. To do so, the steps described above in connection to FIGS. 1A to 1C are implemented. Then, the through vias 118, 124, and the electrical interconnections layers 120 and 126 in the passivation layers 116, 122, and 128, by the same steps as described above for FIG. 1D. However, the through via(s) 118 made in contract with the measurement electrode 112 are placed in the periphery thereof so that later production of a hole 132 through the passivation layers 116, 122, 128, the semiconductor layer 108, and the dielectric layer 106, providing access to the measurement electrode 112, does not damage these interconnections. Areas of electrical insulation, not shown in FIG. 1G, may made in the backing layer 102, under the diamond electrode 112.

In another variant of the sensor 100 previously described in relation to FIG. 1F, it is possible for the electronic circuit 114 to not be made next to the measurement electrode 112, as is the case in FIG. 1F, but rather superimposed over it. In this case, the projection of a section of the first electrode 112 in the (X, Y) plane (X and Y axes represented in FIG. 1F) are superimposed with the projection of a section of the electronic circuit 114, in this same plane. In this case, the electronic circuit 114 is surrounded by the trenches 110 filled with a dielectric material. Such an alternative is possible if the desired size of the electrode 112, as well as the size of the electrical interconnections and the electronic circuit allow.

Figure 2A:
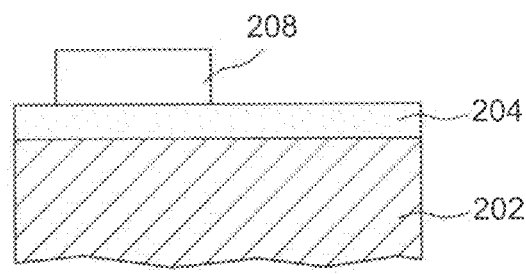
Figure 2B:
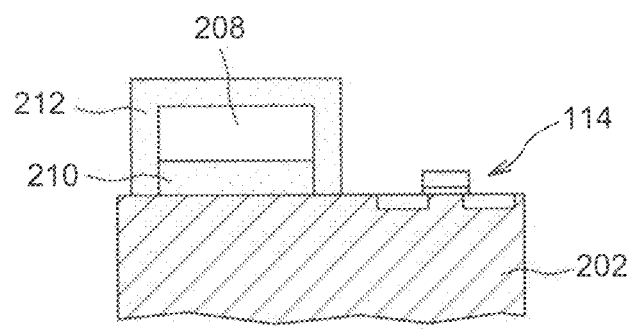
Figure 2C:
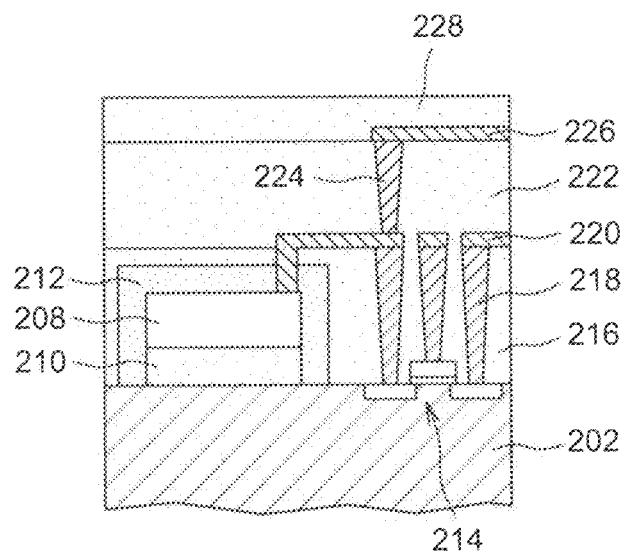
Figure 2D:
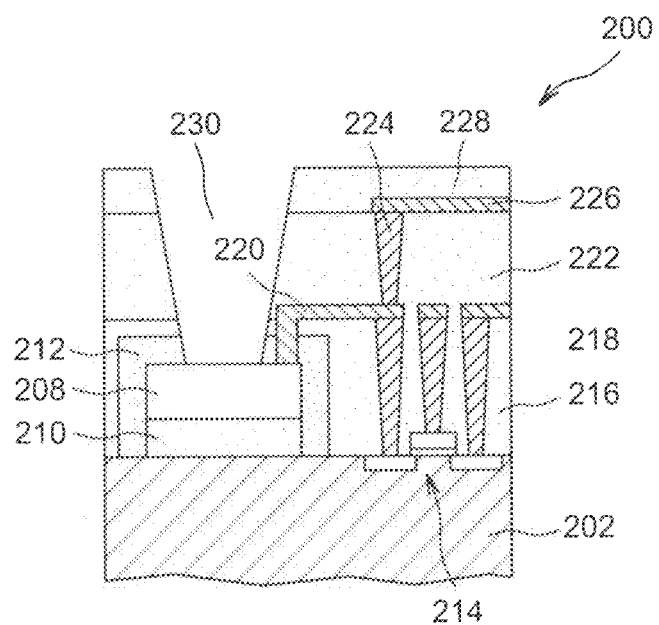

Now we refer to FIGS. 2A and 2D, which show the steps of the production method for an electrochemical measurement biological sensor 200, according to a second embodiment. In these FIGS. 2A and 2D, only the making of part of the biosensor 200 is shown.

In this second embodiment, the device 200 is made from a substrate including a backing layer 202, for example, similar to the backing layer 102 previously described for the biosensor 100, a dielectric layer 204, and a doped diamond layer. The dielectric layer 204 is placed between the doped diamond layer and the backing layer 202. The backing layer 202 has, for example, a thickness of around 700 µm. In one variant, the backing layer 202 may be replaced by layers of a SOI (semiconductor on insulator) substrate, so that the dielectric layer 204, the thickness of which is between 70 nm and 1 µm, is placed between the doped diamond layer and the superficial semiconductor layer of the SOI substrate.

As shown in FIG. 2A, doped diamond electrodes are built on the dielectric layer 204, by etching the doped diamond layer. In FIG. 2A, a single electrode 208, corresponding to the measurement electrode of the biosensor 200, is shown.

The dielectric layer 204 is intended to reduce as much as possible the coupling that may occur between the backing layer 102 and the measurement electrode 208, when a signal is applied to the measurement electrode 208, such coupling being a source of parasitic noise in the measurements made by the biosensor 200. This, the thickness of the dielectric layer 204 may be chosen greater or equal to around 50 nm.

The dielectric layer 204 is then etched in order to only preserve the portions of the dielectric layer 204 located under the biosensor's 200 electrodes, uncovering the surface of the semiconductor in the backing layer 102 located on the side of the electrodes. In the example in FIG. 2B, a remaining portion 210 of the dielectric layer 204 is placed under the measurement electrode 208. A barrier material, for example of a nature similar to that of the barrier layer 106 of biosensor 100 (dielectric material, intrinsic diamond, etc.), enabling prevention of the diffusion of high temperature oxygen in the diamond electrodes during the making of the electronic circuits of the biosensor 200, is located on the doped diamond electrodes of the biosensor 200, forming, in FIG. 2B, a layer 212, of a barrier material covering the measurement electrode 208 and the dielectric portion 210. The layer 212 of barrier material has, for example, a thickness of approximately 1 µm. The electronic circuits in the biosensor 200 are then made in the portions of the backing layer 202 located on the side of the electrodes, by implementation of standard microelectronic steps. In FIG. 2B, a single MOS transistor from an electronic circuit 214 is shown.

Similar to biosensor 100, we then made electrical interconnections on several levels in order to electrically connect the electrodes of the biosensor 200 to the electronic circuit 214. In the example of FIG. 2C, these interconnections are obtained by the passivation layers 216, 222, 228, the through vias 218, 224, and interconnection layers 220, 226, made, for example, in a manner similar to the elements of the biosensor 100.

Finally, the doped diamond electrodes of the biosensor 200, are released by drilling locally, such as by etching, the passivation layers 228, 222, 216, and the barrier material layer 212, making a hole 230, and exposing the upper surface of the measurement electrode 208 (FIG. 2D).

Now, we refer to FIGS. 3A to 3D, which shows the steps of the production method for an electrochemical measurement biological sensor 300, according to a third embodiment. In these FIGS. 3A to 3D, only the production of part of the biosensor 300 is shown.

Figure 3A:
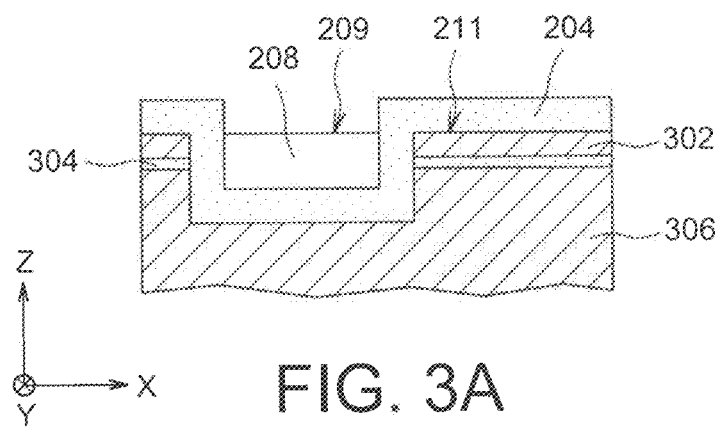
Figure 3B:
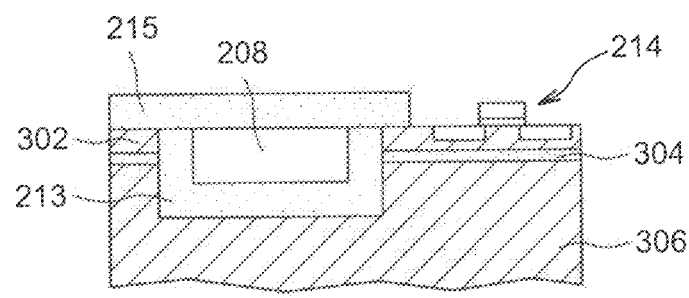

As shown in FIG. 3A, the biosensor 300 is made with a substrate including the dielectric layer 204 placed on the SOI (semiconductor on insulator) substrate layers, including a surface layer 302 composed of a semiconductor materials, a dielectric layer 304, and a massive layer 304, for example, composed of a semiconductor. Recesses are made in the layers 302, 304, and 306 of the SOI substrate, in which the dielectric layer 204 and the doped diamond layer are placed. Portions of this diamond layer which are located in these recesses form the electrodes of the biosensor 300. In FIG. 3A, only one measurement electrode 208 is shown. An upper face 209 of the measurement electrode 208 may therefore be located on the same plane, parallel to the plane (X, Y) shown in FIG. 3A, which is the one in which is located an upper face 211 of the semiconductor surface layer 302.

Figure 3C:
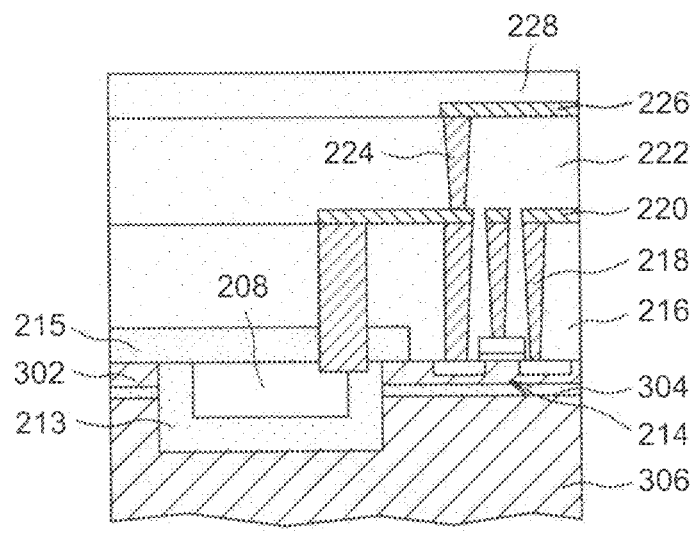
Figure 3D:
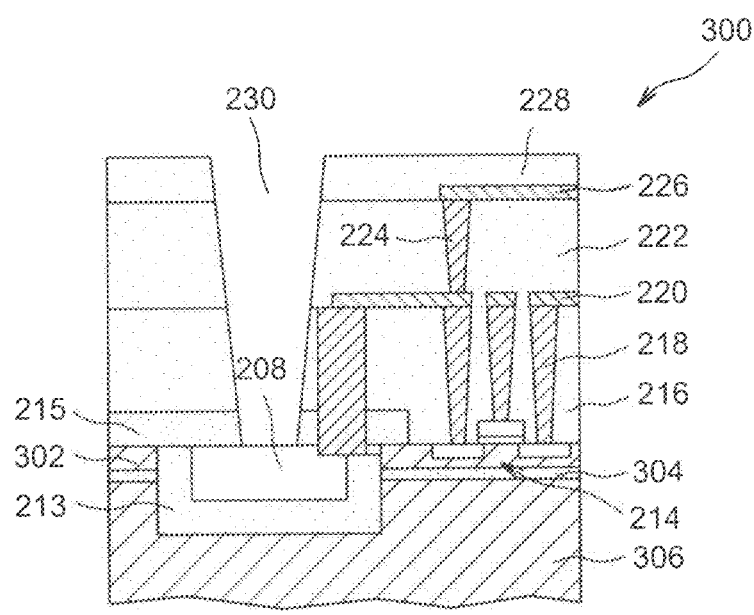

Similar to the production method of the biosensor 200 previously described, we etch portions of the dielectric layer 204, not located under the electrodes. Then we deposit a barrier material 215 to cover especially the measurement electrode 208. We then make the electronic circuits on the biosensor 300 (symbolized by the transistor of an electronic circuit 214 in FIG. 3B) on the surface of the semiconductor layer 302). The electrical interconnections electrically connecting the electrodes to the electronic circuit 214 of the biosensor 300 are then made similar to those previously described for the biosensor 200 (FIG. 3C). Finally, a hole 230 is made through the passivation layers 216, 222, 226, and the barrier layer 215, providing access to the measurement electrode 208.

Compared to biosensor 200, a biosensor such as 300, in which the electrodes are made in the recesses, enables prevention of problems of topology of the surface that may appear if the biosensor electrodes are made above the semiconductor layer 302.

The invention claimed is:

1. A biological sensor for at least one of electrochemical and electrical measurements, comprising:
    a measurement electrode, able to make the at least one of electrochemical and electrical measurements, and including at least a part of a doped diamond layer of a substrate comprising a stack including at least one dielectric layer placed between the doped diamond layer and a semiconductor material layer;
    trenches that delimit the measurement electrode from the remainder of the doped diamond layer, the trenches being filled with at least one dielectric material and crossing at least the doped diamond layer; and
    an electronic circuit for at least one of amplifying and processing at least one electrical signal intended to be issued by the measurement electrode, the electronic circuit being different from the measurement electrode and electrically connected to the measurement electrode and made in a portion of the semiconductor material layer.

2. The biological sensor according to claim 1, in which the substrate is of the SOD type.

3. The biological sensor according to claim 2, in which the semiconductor material layer has a thickness less than or equal to 1 µm, the electronic circuit including one or more transistors of either PD-SOI or FD-SOI type.

4. The biological sensor according to claim 1, in which the electronic circuit is electrically connected to the measurement electrode by through vias and at least one electrical interconnection layer composed of at least one electrically conductive material formed in at least one passivation layer composed of at least one dielectric material placed against the semiconductor material layer, and in which at least one hole made through at least the passivation layer provides an access to the measurement electrode.

5. The biological sensor according to claim 1, in which the measurement electrode is placed in a recess made in at least the semiconductor layer.

6. The biological sensor according to claim 1, in which receptors biologically complementary to the molecules intended to be detected by the sensor are grafted onto the measurement electrode.

7. The biological sensor according to claim 1, further including a second electrode forming a reference electrode, or a second and third electrode, forming respectively a reference electrode and a counter-electrode, each electrode of the sensor including at least a portion of the diamond layer.

8. A biological sensor for at least one of electrochemical and electrical measurements, comprising:
    a measurement electrode, able to make the at least one of electrochemical and electrical measurements, and including at least a part of a doped diamond layer of a substrate comprising a stack including at least one dielectric layer placed between the doped diamond layer and a semiconductor material layer; and
    an electronic circuit for at least one of amplifying and processing at least one electrical signal intended to be issued by the measurement electrode, the electronic circuit being different from the measurement electrode, the electronic circuit being made in a portion of the semiconductor material layer, and the electronic circuit being electrically connected to the measurement electrode by through vias and at least one electrical interconnection layer composed of at least one electrically conductive material made into at least one passivation layer composed of at least one dielectric material, wherein
the semiconductor material layer is placed between the diamond layer and the passivation layer, or
the at least one passivation layer is placed against the semiconductor material layer, at least one hole being made through the at least one passivation layer and providing an access to the measurement electrode from outside of the sensor.

9. The biological sensor according to claim 8, in which the passivation layer is placed between a massive layer forming as a mechanical support for the sensor and the semiconductor layer.

10. The biological sensor according to claim 8, in which the at least one hole is made through the semiconductor material layer and the dielectric layer.

11. A biological sensor for at least one of electrochemical and electrical measurements, comprising:
a measurement electrode, able to make the at least one of electrochemical and electrical measurements, and including at least a part of a doped diamond layer of a substrate comprising a stack including at least one dielectric layer placed between the doped diamond layer and a semiconductor material layer; and
an electronic circuit for at least one of amplifying and processing at least one electrical signal intended to be issued by the measurement electrode, the electronic circuit being different from the measurement electrode, the electronic circuit being made in a portion of the semiconductor material layer, and the electronic circuit being electrically connected to the measurement electrode by through vias and at least one electrical interconnection layer composed of at least one electrically conductive material made into at least one passivation layer composed of at least one dielectric material, wherein
the semiconductor material layer is placed between the diamond layer and the passivation layer, or
the at least one passivation layer is placed against the semiconductor material layer, at least one hole being made through the at least one passivation layer and providing an access to the measurement electrode from outside of the sensor, the at least one hole not being filled with a material.

* * * * *